(12) United States Patent
Cope et al.

(10) Patent No.: US 9,433,161 B2
(45) Date of Patent: Sep. 6, 2016

(54) LARGE SCALE METHOD FOR DISPENSING GRAINS OF POLLEN

(71) Applicant: PIONEER HI-BRED INTERNATIONAL, INC., Johnston, IA (US)

(72) Inventors: Jason M. Cope, Ankeny, IA (US); Todd L. Krone, Johnson, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 335 days.

(21) Appl. No.: 13/672,120

(22) Filed: Nov. 8, 2012

(65) Prior Publication Data

US 2013/0118066 A1 May 16, 2013

Related U.S. Application Data

(60) Provisional application No. 61/558,844, filed on Nov. 11, 2011.

(51) Int. Cl.
*A01B 79/00* (2006.01)
*A01B 79/02* (2006.01)
(Continued)

(52) U.S. Cl.
CPC .................... *A01H 1/025* (2013.01)

(58) Field of Classification Search
CPC ............ A01G 7/06; A01G 7/00; A01H 1/02; A01H 1/00
USPC ...................... 435/420; 47/58.1 R, 58.1, 1.41
See application file for complete search history.

(56) References Cited

U.S. PATENT DOCUMENTS

| 2,669,066 A | 2/1954 | Antles |
| 2,959,358 A | 11/1960 | Vork |

(Continued)

FOREIGN PATENT DOCUMENTS

| CN | 1813521 A | 8/2006 |
| CN | 101743875 A | 6/2010 |

(Continued)

OTHER PUBLICATIONS

Acar, I. et al., *Effect of Pistil Receptivity, Pollen Mixtures, and Pollen Application Distances on Fruit Set of Pistachios (Pistacia vera)*, New Zealand Journal of Crop and Horticultural Science, vol. 36, No. 4, Dec. 1, 2008, pp. 295-300.

(Continued)

*Primary Examiner* — Kent L Bell
(74) *Attorney, Agent, or Firm* — Pioneer Hi-Bred Int'l, Inc.

(57) ABSTRACT

A method is provided for bulk pollination of a plurality of plants. In various embodiments, the method includes collecting a plurality of known grains of pollen, loading the plurality of known grains of pollen into a bulk pollen distributing apparatus, sensing a target pollination location of each of the plurality of plants using an electronic sensor, and distributing the known grains of pollen to the plurality of plants with the bulk pollen distributing apparatus when the electronic sensor senses the target pollination location of each of the plants within a predefined proximity, thereby pollinating the plurality of plants. A plurality of plants may be prepared for controlled pollination by preventing pollination of the plurality of plants by an alternate pollen source. Known grains of pollen may be dispensed to create predetermined gamete crosses with known plants.

20 Claims, 3 Drawing Sheets

(51) Int. Cl.
  *A01C 1/00* (2006.01)
  *A01G 1/00* (2006.01)
  *A01H 3/00* (2006.01)
  *A01H 1/02* (2006.01)

(56) References Cited

U.S. PATENT DOCUMENTS

| | | | |
|---|---|---|---|
| 3,774,845 | A | 11/1973 | Folkert |
| 3,931,914 | A | 1/1976 | Hosaka et al. |
| 3,943,660 | A | 3/1976 | Hosaka |
| 4,087,937 | A | 5/1978 | Meador |
| 4,476,231 | A | 10/1984 | Deindoerfer et al. |
| 4,494,263 | A | 1/1985 | Brown |
| 4,707,931 | A | 11/1987 | Stevenson |
| 4,751,791 | A | 6/1988 | Al-Rawi |
| 4,998,672 | A | 3/1991 | Bordaz et al. |
| 5,066,594 | A | 11/1991 | DeBonte et al. |
| 5,596,838 | A | 1/1997 | Greaves et al. |
| 5,646,846 | A | 7/1997 | Bruce et al. |
| 5,913,915 | A | 6/1999 | McQuinn |
| 5,955,973 | A | 9/1999 | Anderson |
| 6,089,743 | A | 7/2000 | McQuinn |
| 6,122,581 | A | 9/2000 | McQuinn |
| 6,141,904 | A * | 11/2000 | Greaves et al. ........... 47/58.1 R |
| 6,199,000 | B1 | 3/2001 | Keller et al. |
| 6,386,128 | B1 | 5/2002 | Svoboda et al. |
| 6,505,124 | B2 | 1/2003 | Carr et al. |
| 6,505,146 | B1 | 1/2003 | Blackmer |
| 6,510,367 | B1 | 1/2003 | McQuinn |
| 6,516,271 | B2 | 2/2003 | Upadhyaya et al. |
| 6,516,733 | B1 | 2/2003 | Sauder et al. |
| 6,553,299 | B1 | 4/2003 | Keller et al. |
| 6,553,312 | B2 | 4/2003 | Upadhyaya et al. |
| 6,671,698 | B2 | 12/2003 | Pickett et al. |
| 6,672,228 | B1 | 1/2004 | Groelz et al. |
| 6,760,654 | B2 | 7/2004 | Beck |
| 6,810,315 | B2 | 10/2004 | Cessac |
| 6,941,225 | B2 | 9/2005 | Upadhyaya et al. |
| 6,997,120 | B2 | 2/2006 | Gabriel |
| 7,197,992 | B2 | 4/2007 | Gabriel |
| 8,011,133 | B2 | 9/2011 | Sayers |
| 8,220,200 | B2 | 7/2012 | Hunter et al. |
| 8,252,988 | B2 | 8/2012 | Sayers et al. |
| 8,272,162 | B2 | 9/2012 | Lafargue |
| 8,480,011 | B2 | 7/2013 | Endo |
| 8,626,337 | B2 | 1/2014 | Corak et al. |
| 8,857,731 | B2 | 10/2014 | Riera et al. |
| 8,978,298 | B2 | 3/2015 | Sayers et al. |
| 2003/0187560 | A1 | 10/2003 | Keller et al. |
| 2006/0225155 | A1 | 10/2006 | Kumlehn |
| 2006/0278143 | A1 | 12/2006 | Deppermann et al. |
| 2007/0131152 | A1 | 6/2007 | Gabriel |
| 2008/0004778 | A1 | 1/2008 | Rekow |
| 2011/0206241 | A1 | 8/2011 | Sayers et al. |

FOREIGN PATENT DOCUMENTS

| | | |
|---|---|---|
| CN | 102067806 A | 5/2011 |
| CN | 102067808 A | 5/2011 |
| EP | 1 785 032 A2 | 5/2007 |
| FR | 2 866 784 A1 | 9/2005 |
| KR | 20-0196753 Y1 | 9/2000 |
| KR | 10-2004-0037515 A | 5/2004 |
| KR | 10-2010-0006464 A | 1/2010 |
| WO | WO 2012/125593 A2 | 9/2012 |

OTHER PUBLICATIONS

Aylor, D.E., "Quantifying maize pollen movement in a maize canopy", 2005, Agric. For. Meteorol. 131:247-256.

Baltazar, B.M. et al., "Pollination between maize and teosinte: An important determinant of gene flow in Mexico", 2005, Theor. Appl. Genet. 110:519-526.

Bassetti, P. et al., "Floral asynchrony and kernal set in maize quantified by image analysis", 1994, Agron. J. 86:699-703.

Beck, D., *Planting Hybrid Maize*; Seed Course—Chapter 7; Jul. 23, 2002; CIMMYT, Int. , 4 pages.

Bedinger et al., Developmental staging of maize microspores reveals a transition in developing microspore proteins. 1990, Plant Plysiol. 92, pp. 474-479.

Broughton et al., *New Cereal Doubled Haploid Facilities in Western Australia and the status of the Barley Doubled Haploid Program 2001*, Austirlian Barley Technical Symposium [retrieved from the Internet on May 18, 2011] pp. 1-5.

Davies et al., *A comparison of barley isolated microspore and anther culture and the influence of cell culture density*, Plant Cell Reports, (1998) 17: 206-210.

Dukhovnyi, A. E., "The electric charge of maize pollen as a quantitative character" (in Russian). 1975, Kolichestven. priznaki mutantov kukuruzy Kishinev: Stiinca., p. 21-24.

Dukhovny, A. F., *The Electric Charge of Maize Pollenas a Quantitative Character*, Kolichestven, priznski mulantov kukuruzy Kishinev: Stiinca, 1975, pp. 1-3 (English Translation).

Flottum, P. K. et al., "A quantitative sampling method for airborne sweet corn pollen under field conditions" 1984, Crop Sci. 24:375-377.

Fonesca, A. E. et al., "Simulating potential kernel production in maize hybrid seed fields", 2004, Crop Sci. 44:1696-1709.

Fonesca, A. E. et al., "Application of fluorescence microscopy and image analysis for quantifying dynamics of maize pollen shed", 2002, Crop Sci. 42:2201-2206.

Fonesca, A. E., et al., "Tassel morphology as an indicator of potential pollen production in maize [Online]", 2003 Available at: www.plantmanagementnetwork.org/publcm/research/2003/tassle, 15 pages.

Fox et al., Rapid Image Analysis for counting engorged pollen grains of rice. 2001 [oneline], [retrieved on Aug. 17, 2009]. Retrieved from the Internet <http://www.regional.org.au/au/asa/2001/p/5/fox.htm> 3 pages.

Goss, J. A., "Development, physiology, and biochemistry of corn and wheat pollen", 1968, Bot. Rev. 34:333-359.

Hall, A. J. et al., "The effect of water stress and genotype on the dynamics of pollen-shedding and silking in maize", 1982, Field Crops Res. 5:349-363.

Hsu, S. Y. et al., "Relative stage duration of microsporogenesis in maize", 1981, Iowa State *J.* Res. 55:351-373.

Hsu, S. Y. et al., "Development pattern of microspores in *Zea mays* L. The maturation of upper and lower florets of spikelets amound an assortment of genotypes." 1988, Maydica 33:77-98.

Kannely, Preparation and quantification of entomophilous pollen using sonication and an area-counting technique. Madrono, vol. 52, No. 4, pp. 267-269, 2005.

Kiesselbach, T. A., "The structure and reproduction of corn", 1949, Agric. Exp. Stn., Res. Bull. No. 161. Univ. of Nebr. College of Agriculture, Lincoln, NE., pp. 36-49.

Kumar, D. et al., "Correlation between pollen diameter and rate of pollen tube growth in maize (*Zea mays* L.)", 1980, Indian J. Exp. Bot. 18:1242-1244.

Law, S. E. *Agricultural Electrostatic Spray Application: a Review of Significant Research and Development During the 20 $^{th}$ Century*, Journal of Electrostatics, Elseiver Science Publishers B.V. Amsterdam, NL, vol. 51-52, May 1, 2001, pp. 25-42.

Li et al., Impact of pollen grains form Bt transgenic corn on the growth and development of Chinses tussah silkworm, Antheraea pernyi (Lepidoptera: Saturniidae) Environ. Entomol. 34(4): 922-928 (2005).

Mande et al., Fermentation of Bassia Flowers, Industrial and Engineering Chemistry, vol. 41, No. 7, pp. 1451-1454, 1949 [online] [retrieved on Sep. 17, 2009]. Retrieved from the Internet at <http://pubs.acs.org>.

Qiu et al., A simple and effective method for isolating RNA from Alfalfa pollen. Plant Molecular Biology Reporter 12(3) 1994, pp. 209-214.

Russell, K. et al., *Corn Breeding: Lessons from the Past*; Journal of Natural Resources and Life Sciences Education; 2005; vol. 34 http://croptechnology.unl.edu/printLesson.cgi?lessonID-1075412493 Site visited Mar. 17, 2010.

(56) References Cited

OTHER PUBLICATIONS

Sadras, V. O. et al., "Kernel set of the uppermost ear in maize: I. Quantification of same aspects of floral biology", 1985, Maydica 30:37-47.

Sakamoto, D. et al., *Spray Pollination as a Labor-Saving Pollination System in Japanese Pear (Pyrus Pyrifolia (Burm.f.) Nakai): Development of the Suspension Medium*, Scientia Horticulturae, Elseiver Science Publishers, XX, vol. 119, No. 3, Feb. 3, 2009, pp. 280-285.

Tranel, D. M., *Morphology and plasticity of maize (Zea mays L.) male inflorescence development and pollen production*, Dissertation, Iowa State University, DAI-B68/07 (Jan. 2008), pp. 1-100.

Uribelarrea, M. et al., "Pollen production, pollination dynamics, and kernel set in maize", 2002, Crop Sci. 42:1910-1918.

Elvanol as a binder/film former, 2005 [online], [retrieved on Sep. 15, 2009]. Retrieved from the Internet <file://C:\documents and Settings\FOGGLC.DUPONTNET\Desktop\ip_newsite\indpoly_oldsite\elv...>one page.

Ryobi Paint :: 18 Volt ONE+™ Power Paint Sprayer Kit (undated) [online] [retrieved Nov. 8, 2011]. Retrieved from the Internet: <URL: http://www.ryobitools.com/catalog/paint/power_sprayers/P631K1>. 1 page.

Waring Heavy Duty Blender 2001 [online], [retrieved on Sep. 15, 2009]. Retrieved from the Internet <http://web.archieve.org.web/20011120175701/http://productsforhealth.com/waringblender.h...> 3 pages.

International Search Report and Written Opinion for Application No. PCT/US2012/064059 dated Jan. 30, 2013.

U.S. Appl. No. 13/672,179, filed Nov. 8, 2012; In re: Cope et al., entitled *Method for Dispensing Grains of Pollen*.

U.S. Appl. No. 13/099,964 dated May 3, 2011; In re: Sayers et al., In re: *Method and Apparatus of High-Throughput Pollen Extractions, Countingm and Use of Counted Pollen for Characterizing a Plant*.

Office Action for U.S. Appl. No. 13/099,964 dated Sep. 15, 2011.

Office Action for U.S. Appl. No. 12/726,082 dated Dec. 13, 2011.
Notice of Allowance for U.S. Appl. No. 12/726,082 dated Mar. 21, 2012.
Office Action for U.S. Appl. No. 11/823,140 dated Jun. 22, 2010.
Notice of Allowance for U.S. Appl. No. 11/823,140 dated Jan. 14, 2011.
Notice of Allowance for U.S. Appl. No. 11/823,140 dated Jun. 15, 2011.
Office Action for U.S. Appl. No. 11/823,326 dated Oct. 1, 2009.
Office Action for U.S. Appl. No. 11/823,326 dated Jul. 21, 2010.
Office Action for U.S. Appl. No. 11/823,326, dated May 20, 2011.
Office Action for U.S. Appl. No. 11/823,326 dated Sep. 29, 2011.
Notice of Allowance or U.S. Appl. No. 11/823,326 dated Apr. 20, 2012.

Kubersky, U. et al., "Are Pollen Spraying and Pollen Dispensers Alternatives to Conventional Pollination by Bees for Apple Trees?", Erwerbs-Obstbau, 47(5): 117-123, Oct. 2005. (English Abstract).

Lewis, D., "Collection of Pollen and Artificial Wind Pollination", Nature, 3875: 167-168, Feb. 1944.

Philippe, G. et al., "Electrostatic Dusting: an efficient technique of pollination in larch", Annales des Sciences Forestieres, 54(3): 301-310, Jan. 1997.

Vaknin, Y. et al., "The Role of Electrostatic Forces in Pollination", Plant Systematics and Evolution, 222: 133-142, 2000.

European Search Report issued Aug. 22, 2014 for European Patent Application No. 12760235.7, which was filed on Mar. 2012 and published as EP 2688394 on Jan. 29, 2014 (Inventor—Cope; Applicant—Pioneer Hi-Bred International, Inc.) (8 pages).

International Search Report for Application No. PCT/US2012/029739 dated Sep. 24, 2013.

International Search Report for Application No. PCT/US2012/029743 dated Sep. 24, 2013.

Charged Pollen, Feb. 1, 1997, Discover Magazine, http://discovermagazine.com/1997/feb/chargedpollen1065, retrieved from Internet Jun. 14, 2015.

\* cited by examiner

LARGE SCALE METHOD FOR DISPENSING GRAINS OF POLLEN

CROSS REFERENCE TO RELATED APPLICATIONS

The present application claims priority from U.S. Provisional Application No. 61/558,844, filed Nov. 11, 2011, which is hereby incorporated herein in its entirety by reference.

FIELD OF THE INVENTION

Various embodiments of the present invention relate generally to methods and apparatuses for dispensing pollen. More specifically, embodiments of the present invention provide a method configured to dispense pollen using a bulk pollen distributing apparatus.

BACKGROUND OF THE INVENTION

For a variety of reasons, plant species may be intentionally bred. For example, in some applications plant species are intentionally bred to form hybrid plant species. In some applications, hybrid plants are bred to exhibit various desirable traits. Such traits may include, for example, resistance to heat and drought, resistance to disease and insect damage, improved yield characteristics, and improved agronomic quality. In general, plants may be capable of self-pollination, cross-pollination, or both. Self-pollination describes pollination using pollen from one flower that is transferred to the same or another flower of the same plant. Cross-pollination describes pollination using pollen delivered from a flower of a different plant from a different family or line.

Plants that have been self-pollinated and selected for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize (*Zea mays* L.), often referred to as corn in the United States, can be bred by both self-pollination and cross-pollination techniques. Maize has separate male and female flowers on the same plant. The male flowers are located on the tassel and the female flowers are located on the ear. Natural pollination occurs in maize when wind blows grains of pollen from the tassels to the silks that protrude from the tops of the ears.

The development of a hybrid maize variety in a maize seed production program may involve three steps: (1) the selection of plants from various germplasm pools for initial breeding crosses; (2) self-pollination of the selected plants from the breeding crosses for several generations to produce a series of inbred lines, which, individually breed true and are highly uniform; and (3) crossing a selected inbred line with an unrelated inbred line to produce the hybrid progeny. After a sufficient amount of inbreeding successive filial generations will merely serve to increase seed of the developed inbred. Preferably, an inbred line should comprise homozygous alleles at about 95% or more of its loci.

During the maize inbreeding process, vigor of the line may decrease. Vigor may be restored when two different inbred lines are crossed to produce the hybrid progeny. An important consequence of the homozygosity and homogeneity of the inbred lines is that the hybrid between a defined pair of inbreds may be reproduced indefinitely as long as the homogeneity of the inbred parents is maintained. Once the inbreds that create a superior hybrid have been identified, a continual supply of the hybrid seed can be produced using these inbred parents and the hybrid corn plants can then be generated from this hybrid seed supply.

Accordingly, development and production of maize seed may require controlled pollination at one or more steps, as described above.

BRIEF SUMMARY

In one embodiment a method for pollination of one or more plants is provided. In various embodiments the method may include collecting a plurality of known grains of pollen, loading the plurality of known grains of pollen into a bulk pollen distributing apparatus, sensing a target pollination location of each of the one or more plants using an electronic sensor, and distributing the known grains of pollen to the one or more plants with the bulk pollen distributing apparatus, thereby pollinating the plurality of plants. In some embodiments, distributing the known grains of pollen to the one or more plants occurs when the electronic sensor senses the target pollination location of the one or more plants within a predefined proximity. In some embodiments, the one or more plants may comprise one or more corn plants. In some embodiments, the one or more plants may comprise a plurality of plants, and distributing the known grains of pollen with the bulk pollen distributing apparatus may comprise distributing the known grains of pollen with a field sprayer.

Some embodiments may further comprise preparing the one or more plants for controlled pollination by preventing pollination of the one or more plants by an alternate pollen source. In some embodiments, the one or more plants may comprise one or more corn plants, and preventing pollination of the one or more plants by an alternate pollen source may comprise covering a plurality of silks of the one or more corn plants. In some embodiments, the one or more plants may comprise one or more corn plants, and preventing pollination of the one or more plants by an alternate pollen source may comprise detasseling the one or more corn plants. In some embodiments, preventing pollination of the one or more plants by an alternate pollen source may comprise genetically sterilizing the one or more plants so that the plurality of plants do not produce viable pollen. In some embodiments, the one or more plants may comprise one or more corn plants, and preventing pollination of the one or more plants by an alternate pollen source may comprise genetically predisposing the one or more corn plants to begin silk emergence at a first time and to begin shedding pollen at a second time, wherein the first time and the second time differ.

Some embodiments may further comprise planting the one or more plants in a crop production plot, which, in some embodiments, may comprise planting a first plurality of plants in a crop production plot. Some embodiments may further comprise planting a second plurality of plants in a pollen production plot from which the known grains of pollen are collected. In some embodiments, the crop production plot may be separate from the pollen production plot. In some embodiments, the second plurality of plants may be genetically configured to shed the known grains of pollen before at least one of silk emergence of the first plurality of plants or pollen shedding of the first plurality of plants. In some embodiments, the one or more plants may comprise one or more known plants, and distributing the known grains of pollen may comprise pollinating the one or more known plants to create a predetermined gamete cross. In some embodiments, the one or more plants may comprise a plurality of plants, and distributing the known grains of pollen with the pollen distributing apparatus may comprise distributing the known grains of pollen through a manifold configured to direct the known grains of pollen to two or more rows of the plurality of plants. Some embodiments may further comprise preserving the known grains of pollen prior to distributing the known grains of pollen. In some embodiments, preserving the known grains of pollen comprises controlling a humidity level to which the known grains of pollen are exposed.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Controlled pollination of plants, for example during cross-pollination, may involve manually collecting and dispensing pollen. Manually collecting and dispensing pollen may be very labor intensive. For example, a worker may manually collect pollen by knocking it off of the tassels of the ear corn into a tassel bag. Further, the worker may then manually sprinkle the pollen onto the silks of an ear of corn which has been covered with a shoot bag so as to prevent pollination with pollen other than the collected grains of pollen. Thus, collection of pollen and controlled pollination using the collected pollen may involve many manual steps that may be conducted over the course of one or more days. Further, application of pollen using tassel bags may not efficiently make use of the collected pollen since the tassel bag may not allow for targeted application of the pollen in an easily controlled manner. Thus, workers may tend to apply more of the pollen than would otherwise be necessary. Accordingly, embodiments of the invention provide improved apparatuses and methods for dispensing pollen to a plurality of plants.

The following description relates to an embodiment in which pollen is distributed to a plurality of plants; however, in other embodiments the present invention contemplates using one or more of the aspects described herein to distribute pollen to an individual plant. As such, in various embodiments a bulk pollen distributing apparatus may comprise a single pollen applicator or a plurality of pollen applicators. Thus, the present invention provides methods for facilitating automated, semi-automated, or manual pollinations of individual plants or a plurality of plants, either with a single pollen applicator or with a plurality of pollen applicators.

Figure 1:
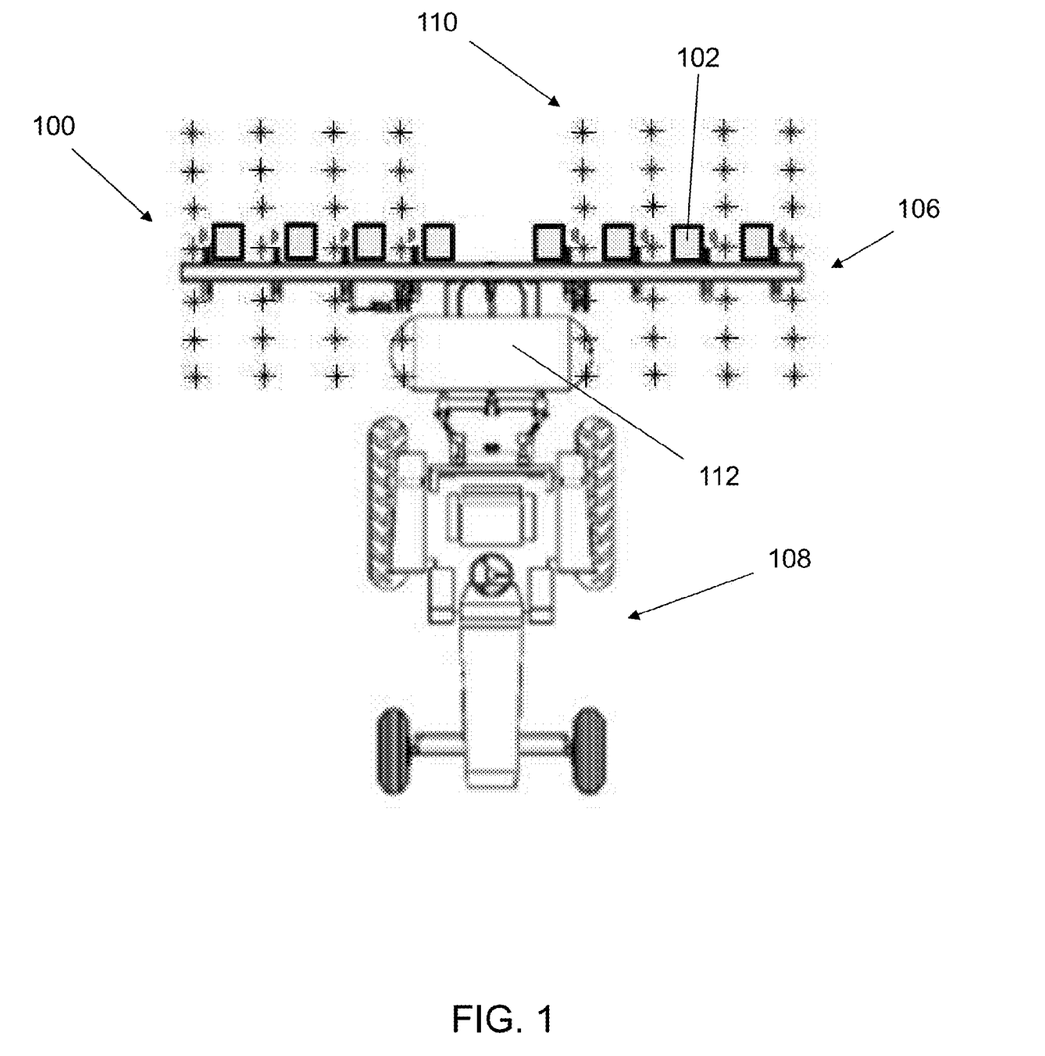
FIG. 1 illustrates an embodiment of a bulk pollen distributing apparatus configured for dispensing grains of pollen in accordance with an example embodiment of the present invention.

FIG. 1 illustrates an embodiment of a bulk pollen distributing apparatus 100 configured for dispensing grains of pollen. In the depicted embodiment, the bulk pollen distributing apparatus 100 comprises a plurality of pollen applicators 102.

In the depicted embodiment, the plurality of pollen applicators 102 are attached to a mobile carrier 106 (such as, for example, a field sprayer) configured to be transported through a field using a mobile transport device 108, such as, for example, a farm tractor, as in the depicted embodiment. Other examples of a mobile transport device may include but are not limited to, an all terrain vehicle, one or more horses, a multipurpose vehicle such as a Unimog or Humvee, etc. In other embodiments, the mobile carrier 106 may be self-propelled, such as, for example, by including an integrated transporting mechanism or device.

In various embodiments, the pollen applicators 102 are configured to apply pollen grains to a plurality of plants 110, such as those planted in an agricultural plot. As will be described below, in some embodiments the grains of pollen may be known. In the depicted embodiment, a plurality of pollen grains is stored in a storage container 112, which is carried by the mobile transport device 108. In other embodiments, the storage container 112 may be located on the bulk pollen distributing apparatus 100. In still further embodiments, one or more of the pollen applicators 102 may include dedicated pollen storage containers, such that one or more of the pollen applicators 102 may distribute differing types of pollen. In some embodiments, the dedicated pollen storage containers may be located, for example, on the mobile transport planting device 108, on the mobile carrier 106, and/or proximate the pollen applicators 102.

In the depicted embodiment, pollen grains from the storage container 112 are delivered to the each of the plurality of pollen applicators 102 through individual tubes (not shown) via a manifold of the mobile carrier 106. Although in the depicted embodiment the pollen grains are transported from the storage container 112 to the plurality of pollen applicators 102 using pressurized air, in other embodiments the pollen grains may be delivered to the pollen applicators 102 through a variety of other means, including, but not limited to, gravity-based or other mechanical distribution systems. In other embodiments, pollen may be distributed using one or a combination of various forces including, but not limited to, positive pressure forces, negative pressure forces, mechanical modes of action, centrifugal force, and hydraulic, pneumatic, and gravity forces.

Figure 2:
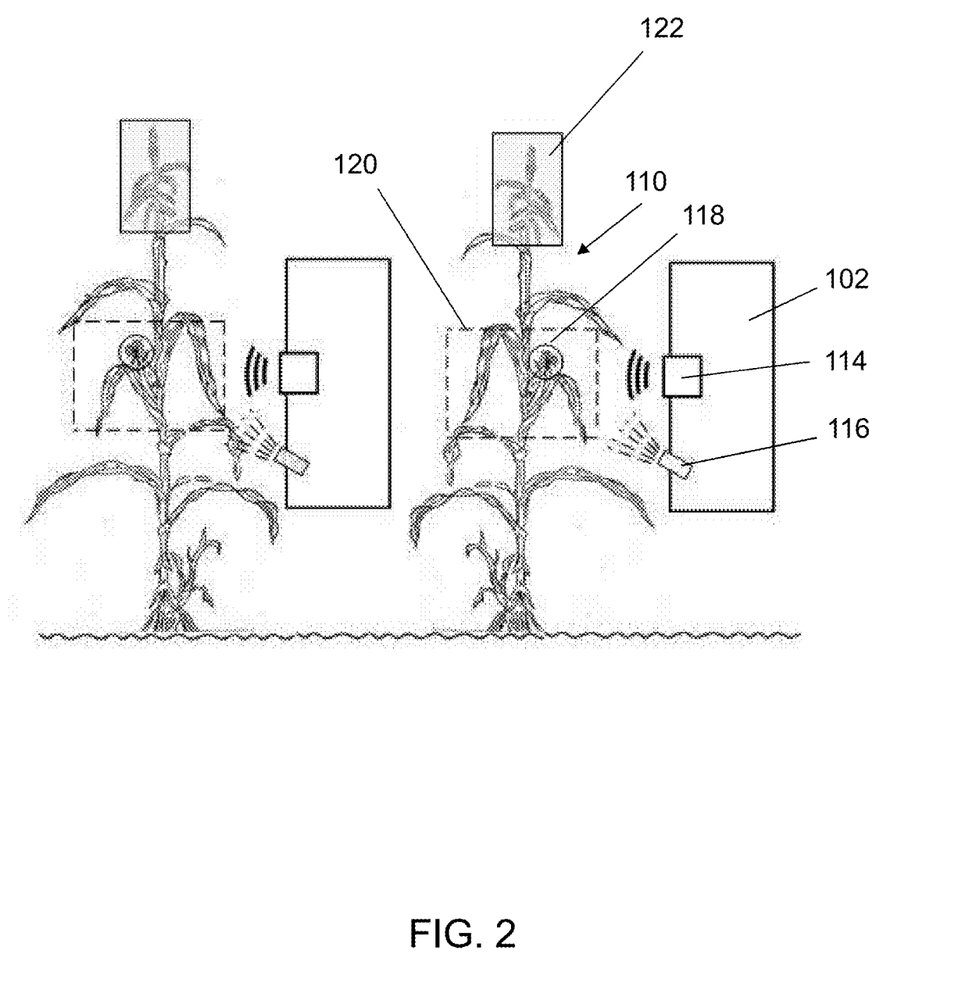
FIG. 2 illustrates an example of pollen applicators as may be embodied on a bulk pollen distributing apparatus in accordance with an example embodiment of the present invention.

FIG. 2 shows an example of two pollen applicators 102 as may be embodied on a bulk pollen distributing apparatus 100 in accordance with an example embodiment of the present invention. In the depicted embodiment, each of the pollen applicators 102 includes a sensor 114 and a spray nozzle 116. In various embodiments, the sensor 114 is configured to sense a target pollination location 118 on a plant. In the depicted embodiment, the target pollination location 118 comprises the female silks of a corn plant. It should be noted that although in the depicted embodiment, the plurality of plants 110 comprise corn plants, in other embodiments the plurality of plants could comprise a variety of other plants. For example, in various embodiments the present invention may be utilized for any number of crops which are or can be pollinated via wind, air, gravity, etc., including, but not limited to, sorghum, soybeans, canola and various other fruit and vegetable crops. In such a manner, the characteristics of a target pollination location may vary and thus may be configured to suit a particular application. In the depicted embodiment, the sensor 114 is an electronic optical sensor, however in other embodiments the sensor 114 may be any other sensor configured to sense a target pollination location on a plant.

The majority of monocultures rely heavily upon gravity, wind and/or insect based pollination in order to give rise to fruits and/or seedlings. Thus, there is an advantage to being able to harvest pollen and target it for direct application on female organelles, and, in some embodiments, in a time period that finds the female plant organelles at a prime point of fertility.

In the depicted embodiment, the sensors 114 are in communication with one or more controllers (not shown) configured to control and process data received by the sensors 114. The nozzles 116 are also in communication with the one or more controllers. As such, the spray nozzles 116 of the bulk pollen distributing apparatus 100 are further configured to be controlled to direct grains of pollen into target pollination locations 118 of the plants 110. In the depicted embodiment, each of the spray nozzles 116 has a fixed orientation with respect to its respective sensor 114 and is configured to direct grains of pollen into a respective target pollination location 118. In various embodiments, the controller may control each spray nozzle to direct grains of pollen into the respective target pollination locations 118 when the sensor 114 senses the target pollination location 118 of the plant within a predefined proximity (depicted as area 120). In other embodiments, the spray nozzles 116 may be automatically positionable such that their orientation (e.g., spray position) may be controlled by the one or more controllers. In such a manner, one or more of the spray nozzles 116 may be controlled to change their respective spray position in order to direct pollen into a respective target pollination location 118 as sensed by the sensor 114.

In some embodiments, the bulk pollen distributing apparatus 100 may be configured to apply an electrical charge to the grains of pollen dispensed through the nozzles 116. For example, an electrode may be positioned in the storage container 112. In various embodiments, the electrode may be configured to impart a charge on the grains of pollen as they are dispensed from the storage container 112. In other embodiments, each pollen applicator 102 may include an electrode, such as, for example, proximate an outlet of each nozzle 116 in order to impart an electrical charge on the pollen grains. The electrical charge imparted by the electrode may be, for example, configured to attract the grains of pollen to silks of a corn plant to which the grains of pollen are applied. Accordingly, applying an electrical charge to the pollen may facilitate pollination. However, not all embodiments of the bulk pollen distributing apparatus 100 may apply an electrical charge to the grains of pollen, and pollination may occur without application of an electrical charge.

Additionally, the bulk pollen distributing apparatus 100 may further comprise an environmental control mechanism configured to control an environmental condition within the storage container 112. For example, the environmental condition may comprise temperature, humidity, light exposure, and/or other environmental conditions. Thereby, the bulk pollen distributing apparatus 100 may comprise a heating element, condenser, or other environmental control mechanism configured to heat or cool the grains of pollen in the storage container 112. In one embodiment the environmental control mechanism may comprise a jacket configured to partially or fully surround the storage container 112. The jacket may be heated or cooled so as to control the temperature within the storage container 112 to achieve a desired temperature of the grains of pollen therein and thereby maintain viability of the grains of pollen. Further a fan, the condenser, or a separate dehumidifier may be employed to regulate humidity within the storage container 112.

With regard to light exposure, a coating may be applied to the storage container 112 to reduce visible, ultraviolet, and/or infrared light transmission through the storage container 112 to the grains of pollen. Alternatively, the material from which the storage container 112 is formed may be selected to limit light transmission. Accordingly, one or more conditions within the storage container 112 may be regulated. Thereby, for example, the viability of the grains of pollen may be maintained for an extended period of time. Alternatively or additionally, the environmental conditions may be controlled in a manner that facilitates dispensing of the grains of pollen and/or improves adhesion of the grains of pollen to the plant to which the grains of pollen are applied.

Methods for dispensing grains of pollen will now be described. While the description may generally describe operations conducted by embodiments of the bulk pollen distributing apparatus 100 illustrated in FIGS. 1 and 2, it should be understood that this is for purposes of brevity only. In this regard, various other apparatus embodiments may be employed to conduct the methods that will be described below.

Figure 3:
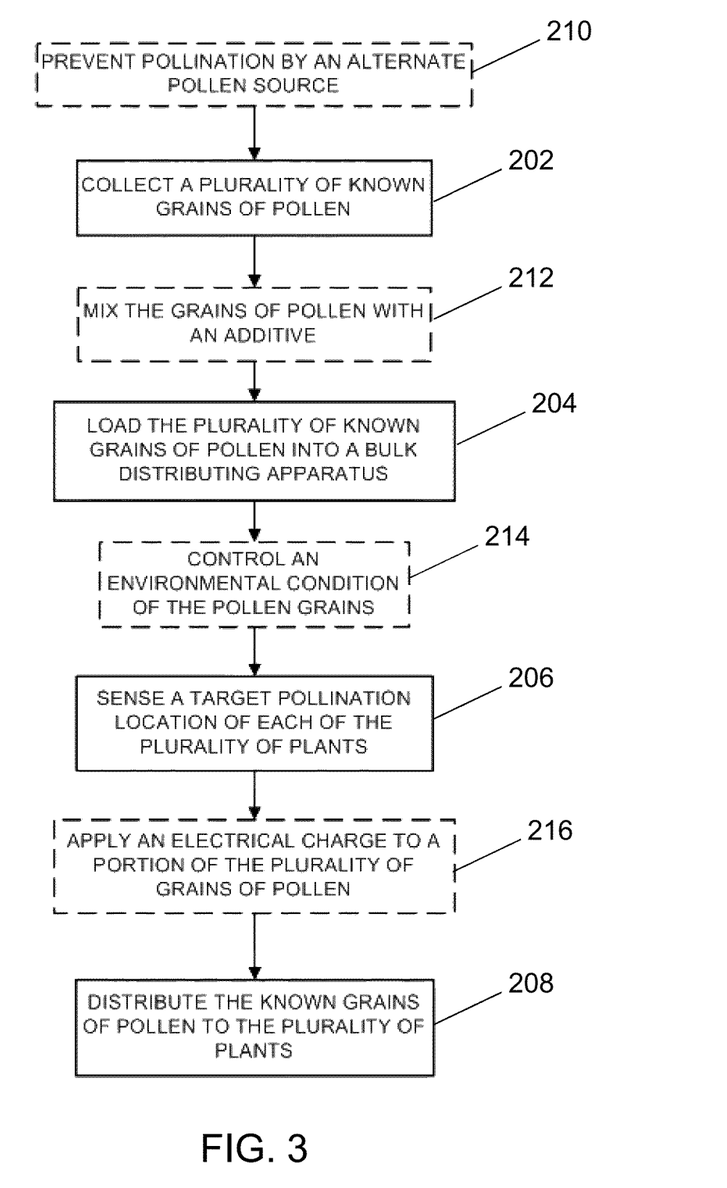
FIG. 3 illustrates a method for bulk pollination of a plurality of plants in accordance with an example embodiment of the present invention.

FIG. 3 illustrates a method for bulk pollination of a plurality of plants in accordance with an example embodiment of the present invention. As illustrated, the method may comprise collecting a plurality of known grains of pollen at operation 202. Known grains of pollen may comprise grains of pollen for which characteristics of the grains of pollen are known. For example, the specific plant from which the grains of pollen are collected may be known, the genetic make-up of the grains of pollen may be known, and/or the plot from which the grains of pollen are collected may be known. Similarly, a known plant may refer to a plant for which the genetic make-up or other characteristics of the plant are known. Collecting pollen may comprise knocking pollen off of tassels of ear corn into a tassel bag, vacuuming the pollen off of the tassels, and/or any other method of collecting pollen as may be understood by one having skill in the art.

The method may also comprise loading the plurality of grains of pollen into a bulk distributing apparatus at operation 204. In some embodiments the pollen may be stored prior to loading the plurality of grains of pollen into a bulk distributing apparatus. The method may also comprise sensing a target pollination location of each of the plurality of plants at operation 206. As noted above, in some embodiments this may be accomplished using an electronic sensor, such as an optical sensor. Additionally, the method may comprise distributing the known grains of pollen to the plurality of plants at operation 208. As noted above, in some embodiments this may occur when the sensor senses the target pollination location of the plant within a predefined proximity.

In some embodiments the method may additionally or alternatively comprise other operations including those operations illustrated in dashed lines in FIG. 3. For example, the method may further comprise preventing pollination by an alternate pollen source at operation 210. In some embodiments, the plurality of plants may be corn plants and this may accomplished by covering a plurality of silks of the corn plants prior to pollinating the corn plants with the bulk pollen distributing apparatus, as illustrated by bags 122 in FIG. 2. Thereby, it may be more likely that pollination occurs with the grains of pollen propelled from the pollen applicators rather than with other grains of pollen from alternate pollen sources. In other embodiments wherein the plurality of plants are corn plants, preventing pollination of the plurality of plants by an alternate pollen source may comprise detasseling the plurality of corn plants, genetically sterilizing the plurality of plants so that the plurality of plants do not produce viable pollen, and/or genetically predisposing the plurality of corn plants to begin silk emergence at a first time and to begin shedding pollen at a second time, wherein the first time and the second time differ. In other embodiments, the plurality of plants may be planted in a crop production plot and a second plurality of plants (which may be separate from the first plurality of plants) may be planted in a pollen production plot from which the known grains of pollen are collected. In some embodiments, the second plurality of plants may be genetically configured to shed the known grains of pollen before at least one of silk emergence of the first plurality of plants or pollen shedding of the first plurality of plants.

The method may also include mixing the grains of pollen with an additive at operation 212, which may occur prior to distributing the grains of pollen at operation 208. The additive may be configured to enhance visibility of the plurality of grains of pollen distributed by the bulk pollen distributing apparatus in some embodiments. For example, the additive may comprise a white talcum powder, or other substance that is easily visible. Thereby, an operator may be able to see the flow rate of the grains of pollen as they are distributed and further the operator may see the amount of pollen that lands on the plant (as represented by the additive). For example, the grains of pollen and additive may be mixed in a one-to-one ratio (by mass or volume) in some embodiments. The additive may additionally or alternatively be configured to control a moisture level of the plurality of grains of pollen. For example, the additive may increase the duration of viability of the grains of pollen by providing moisture to the grains of pollen. In this regard, the additive may store and release moisture.

Additionally, the method may comprise controlling an environmental condition within the pollen storage container at operation 214. As described above, in some embodiments the environmental condition may comprise temperature, humidity, and/or light exposure in some embodiments, although various other environmental conditions may be controlled in other embodiments. In addition, the method may include applying an electrical charge to a portion of the plurality of grains of pollen at operation 216. Thereby, the binding potential of the grains of pollen with the plant may be increased.

By employing the methods and/or the bulk pollen distributing apparatus 100 disclosed herein, the grains of pollen may be applied in a relatively more efficient manner than may be accomplished by manually applying the pollen with a tassel bag. In particular, the bulk pollen distributing apparatus 100 (or other distributing devices in accordance with the disclosure herein) may selectively propel the pollen onto the plant in a controlled manner. Further, the pollen may be propelled directly at the desired target pollination location of the plant so as to more effectively use the grains of pollen, and potentially lead to greater pollination rates. By selectively directing pollen in this manner, less pollen may be required to pollinate the same number of plants as compared to application of the pollen using tassel bags. Additionally, selectively directing pollen in this manner may cause the pollen to pollinate only the target plant, since the direction in which the pollen are directed and the quantity thereof may be carefully controlled using the bulk pollen distributing apparatus 100.

As noted above, in some embodiments pollinating the plant with the portion of the plurality of grains of pollen may comprise pollinating a known plant with known grains of pollen to create a predetermined gamete cross. Thus, knowledge of the characteristics of the pollen and the plant to which the pollen is applied may be employed to create a known cross in some embodiments. However, in other embodiments pollinating the plant with the portion of the plurality of grains of pollen may comprise pollinating an unknown plant and/or pollinating a plant with plurality of unknown grains of pollen to create a gamete cross. In this regard, in some embodiments the characteristics of the cross may not be completely known at the time of pollination.

As noted above, in other embodiments an individual plant may be pollinated using one or more of the aspects described herein. As such, the present invention also covers pollination of an individual plant by collecting a plurality of known grains of pollen, loading the plurality of known grains of pollen into a pollen distributing apparatus, sensing a target pollination location of the plant using an electronic sensor, and distributing the known grains of pollen to the plant with the pollen distributing apparatus. In some embodiments, the known grains of pollen are distributed to the plant when the electronic sensor senses the target pollination location within a predefined proximity.

Many modifications and other embodiments of the invention set forth herein will come to mind to one skilled in the art to which these invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for pollination of one or more plants, comprising:

collecting a plurality of known grains of pollen;

loading the plurality of known grains of pollen into a bulk pollen distributing apparatus;

preparing the one or more plants for controlled pollination by preventing pollination of the one or more plants by an alternate pollen source;

sensing a target pollination location of each of the one or more plants using an electronic sensor; and distributing the known grains of pollen to the one or more plants with the bulk pollen distributing apparatus, thereby pollinating the one or more plants.

2. The method of claim 1, wherein distributing the known grains of pollen to the one or more plants occurs when the electronic sensor senses the target pollination location of the one or more plants within a predefined proximity.

3. The method of claim 1, wherein the one or more plants comprises one or more corn plants.

4. The method of claim 1, wherein the one or more plants comprises a plurality of plants, and wherein distributing the known grains of pollen with the bulk pollen distributing apparatus comprises distributing the known grains of pollen to the plurality of plants with a field sprayer.

5. The method of claim 1, wherein the one or more plants comprises one or more corn plants, and
wherein preventing pollination of the one or more plants by an alternate pollen source comprises covering silks of the one or more corn plants.

6. The method of claim 1, wherein the one or more plants comprises one or more corn plants, and
wherein preventing pollination of the one or more plants by an alternate pollen source comprises detasseling the one or more corn plants.

7. The method of claim 1, wherein preventing pollination of the one or more plants by an alternate pollen source comprises genetically sterilizing the one or more plants so that the one or more plants do not produce viable pollen.

8. The method of claim 1, wherein the one or more plants comprises one or more corn plants, and
wherein preventing pollination of the one or more plants by an alternate pollen source comprises genetically predisposing the one or more corn plants to begin silk emergence at a first time and to begin shedding pollen at a second time, wherein the first time and the second time differ.

9. The method of claim 1, further comprising planting the one or more plants in a crop production plot.

10. The method of claim 9, wherein the one or more plants comprises a first plurality of plants, and further comprising planting a second plurality of plants in a pollen production plot from which the known grains of pollen are collected.

11. The method of claim 10, wherein the crop production plot is separate from the pollen production plot.

12. The method of claim 10, wherein the second plurality of plants are genetically configured to shed the known grains of pollen before at least one of silk emergence of the first plurality of plants or pollen shedding of the first plurality of plants.

13. The method of claim 1, wherein the one or more plants comprises one or more known plants, and
wherein distributing the known grains of pollen comprises pollinating the one or more known plants to create a predetermined gamete cross.

14. The method of claim 1, wherein the one or more plants comprises a plurality of plants, and distributing the known grains of pollen with the pollen distributing apparatus comprises distributing the known grains of pollen through a manifold configured to direct the known grains of pollen to two or more rows of the plurality of plants.

15. The method of claim 1, further comprising preserving the known grains of pollen prior to distributing the known grains of pollen.

16. The method of claim 15, wherein preserving the known grains of pollen comprises controlling a humidity level to which the known grains of pollen are exposed.

17. A method for pollination of one or more corn plants, comprising:
collecting a plurality of known grains of pollen;
loading the plurality of known grains of pollen into a bulk pollen distributing apparatus;
preparing the one or more corn plants for controlled pollination by covering silks of the one or more corn plants to prevent pollination of the one or more corn plants by an alternate pollen source;
sensing a target pollination location of each of the one or more corn plants using an electronic sensor, and
distributing the known grains of pollen to the one or more corn plants with the bulk pollen distributing apparatus, thereby pollinating the one or more corn plants.

18. A system for pollinating one or more plants, comprising:
a bulk pollen distributing apparatus configured to receive a plurality of known grains of pollen, wherein the bulk pollen distributing apparatus comprises an electronic sensor configured to sense a target pollination location of each of the one or more plants, wherein the bulk pollen distributing apparatus is configured to distribute the known grains of pollen to the one or more plants to pollinate the one or more plants; and
means for preventing pollination of the one or more plants by an alternate pollen source.

19. The system of claim 18, wherein the one or more plants comprise one or more corn plants, and wherein the means for preventing pollination of the one or more plants by an alternate pollen source is selected from the group consisting of:
one or more bags, wherein the one or more bags are configured to cover silks of the one or more corn plants;
means for detasseling the one or more corn plants;
means for genetically sterilizing the one or more corn plants so that the one or more corn plants do not produce viable pollen; and
means for genetically predisposing the one or more corn plants to begin silk emergence at a first time and to begin shedding pollen at a second time, wherein the first time and the second time differ.

20. The system of claim 19, wherein the bulk pollen distributing apparatus comprises:
a mobile carrier;
at least one storage container configured to receive the known grains of pollen; and
a plurality of pollen applicators attached to the mobile carrier and positioned in communication with the at least one storage container, wherein each pollen applicator of the plurality of pollen applicators comprises a respective electronic sensor and a spray nozzle, wherein each respective electronic sensor of the plurality of pollen applicators is configured to sense a target pollination location on a corn plant of the one or more corn plants, and wherein the plurality of pollen applicators are configured to receive the known grains of pollen from the at least one storage container and to apply the known grains of pollen to the one or more corn plants through the spray nozzles of the plurality of pollen applicators.

\* \* \* \* \*